US00PP26816P3

(12) United States Plant Patent
Bédard

(10) Patent No.: US PP26,816 P3
(45) Date of Patent: Jun. 14, 2016

(54) SHRUB ROSE PLANT NAMED 'WEKYOOPEDKO'

(50) Latin Name: *Rosa hybrida*
Varietal Denomination: WEKyoopedko

(71) Applicant: Early Morning LLC, Pomona, CA (US)

(72) Inventor: Christian Bédard, Placentia, CA (US)

(73) Assignee: EARLY MORNING LLC, Pomona, CA (US)

( * ) Notice: Subject to any disclaimer, the term of this patent is extended or adjusted under 35 U.S.C. 154(b) by 79 days.

(21) Appl. No.: 14/121,989

(22) Filed: Nov. 12, 2014

(65) Prior Publication Data

US 2016/0135337 P1 May 12, 2016

(51) Int. Cl.
*A01H 5/02* (2006.01)

(52) U.S. Cl.
USPC ..... Plt./102

(58) Field of Classification Search
USPC ..... Plt./102, 108
See application file for complete search history.

(56) References Cited

U.S. PATENT DOCUMENTS

PP16,202 P2 1/2006 Radler

*Primary Examiner* — Anne Grunberg
(74) *Attorney, Agent, or Firm* — McKee, Voorhees & Sease, PLC

(57) ABSTRACT

A new variety of Shrub rose suitable for garden decoration, having flowers of red with lighter reverse coloration with a white 'eyezone'.

1 Drawing Sheet

Classification: The present invention relates to a new *Rosa hybrida* plant.

Variety denomination: The new plant has the varietal denomination 'WEKyoopedko'.

BACKGROUND OF THE INVENTION

This invention relates to a new and distinct variety of Shrub Rose. It has as its seed parent the variety known as 'WEKiscorou' (not patented) and as its pollen parent the variety known as 'RADtko' (U.S. Plant Pat. No. 16,202).

SUMMARY OF THE INVENTION

Among the features which distinguish the new variety from other presently available and commercial rose cultivars known to the inventor are the following combinations of characteristics: its high degree of resistance to black spot, powdery mildew, downy mildew and rust, its excellent color stability throughout the life of the flower and its rough peduncle with many stipitate glands and some small prickles. The plant has an upright bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKyoopedko' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKiscorou' by the following combination of characteristics: whereas 'WEKyoopedko' bears flowers of red with lighter reverse coloration with a white 'eyezone', 'WEKiscorou' bears flowers of scarlet coloration with a white reverse. The new variety has an upright bushy medium height growing habit (about 110 to about 142 cm. in height), whereas the seed parent has a compact rounded significantly shorter growing habit (about 30 to about 45 cm. in height).

The new variety may be distinguished from its pollen parent, 'RADtko' by the following combination of characteristics: whereas 'WEKyoopedko' bears flowers of red with lighter reverse coloration with a white 'eyezone', 'RADtko' bears flowers of red coloration. The new variety has an upright bushy medium height growing habit (about 110 to about 142 cm. in height), whereas the pollen parent has a rounded bushy significantly shorter growing habit (about 90 to about 120 cm. in height).

COMPARISON WITH THE CLOSEST COMMERCIALLY AVAILABLE CULTIVAR

The closest commercially available cultivar to the new variety is the pollen parent 'RADtko' (U.S. Plant Pat. No. 16,202).

BRIEF DESCRIPTION OF ILLUSTRATION

The accompanying photograph illustrates the new variety and shows the flowering thereof from bud to full bloom depicted in color as nearly correct as it is possible to make in a color illustration of the character.

The branches used for the photograph came from 3 to 4 year-old rose plants of the new variety grown outdoors in Wasco, Calif. in the month of October.

Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, Calif. in the month of October. Phenotypic expression may vary with environmental, cultural and climatic conditions, as well as differences in conditions of light and soil.

FLOWER

The new variety sometimes bears its flowers singly, usually in clusters of two to four per stem. Flowers may be borne in regular rounded clusters on strong somewhat short to medium length stems (about 18 to about 65 cm.). Outdoors, the plant blooms abundantly and nearly continuously during the growing season. The flowers have a slight tea fragrance.

BUD

The peduncle is about 2.1 to about 5.8 cm. in length, of moderately heavy caliper (about 0.2 to about 0.3 cm. in diameter), and usually erect. It is rough, with many stipitate glands and some small prickles. Peduncle color is between 144A and 146C often heavily suffused, especially on the side exposed to the sun, with between 187B and 187A.

Before the calyx breaks, the bud is about 0.8 to about 1.5 cm. in diameter at the widest point, about 1.4 to about 1.8 cm. in length, and pointed to somewhat ovoid in shape. The surface of the bud bears between 6 to 12 foliaceous appendages and some stipitate glands, usually with slender moderately cut foliaceous parts extending beyond the tip of the bud about ½ or more of its length. Bud color is between 137C and 146C often heavily suffused, especially on the side exposed to the sun, with between 187A and 187B.

The sepals are about 2.0 to about 2.7 cm. in length and about 0.6 to about 0.8 cm. in width at the widest point. The outer surface color of the sepal is between 137C and 146C often heavily suffused, especially on the side exposed to the sun, with between 187A and 187B. The outer surface of the sepal is somewhat rough and bears between 0 to 5 foliaceous appendages with some stipitate glands. The inner surface color of the sepal is near 146C broadly bordered by near 137B. After the sepals open, the inner surface color is often moderately suffused, especially on the area exposed to the sun, with between 187A and 187B. The inner surface of the sepal is covered with fine wooly tomentum; sepal margins are lined with some stipitate glands and many hairs.

The receptacle of the flower is of medium length (about 0.5 to about 0.7 cm.) and average in caliper (about 0.6 to about 0.8 cm. in diameter). The receptacle is urn-shaped in form. Its surface is smooth with moderately thick fleshy walls. The receptacle color is between 144A and 146C.

As the petals open (after the calyx breaks), the bud is about 1.5 to about 1.9 cm. in diameter at the widest point, about 1.9 to about 2.3 cm. in length, and ovoid to somewhat pointed in form. The color of the under surfaces of the newly opened petals is between 53A and 53B. At the point where the petal attaches, there is a large zone of between 1C and 154C. The color of the upper surfaces of the newly opened petals is between 187A and 187B. At the point where the petal attaches, there is a large zone of between 1C and 154C.

BLOOM

When fully open, the bloom ranges from about 5.6 to about 8.9 cm. in diameter. Petalage is double with about 15 to 24 petals and about 2 to 6 petaloids irregularly arranged. When partially open, the bloom form is high centered to somewhat cupped, and the petals are moderately tightly spiraled to somewhat cupped with petal edges somewhat reflexed outward. When fully open, the bloom form is more cupped, and the petals are loosely cupped to somewhat undulated with petal edges moderately reflexed outward.

PETALS

The substance of the petals is heavy and of moderately thick thickness, with upper surfaces moderately satiny to somewhat velvety and under surfaces slightly shiny. The petals are about 2.8 to about 4.3 cm. in length and about 2.4 to about 4.4 cm. in width at the widest point. Petal margins are entire.

The outer petals are somewhat obovate to nearly round in shape with rounded apices.

The inner petals are moderately obovate in shape with rounded apices.

Petaloids are about 1.0 to about 3.7 cm. in length and about 0.5 to about 2.4 cm. in width at the widest point. Petaloids are irregularly shaped moderately oblanceolate to somewhat obovate with rounded apices.

NEWLY OPENED FLOWER

The under surface color of the outer, intermediate and inner petals is between 155A and 155B often moderately to heavily suffused with between 53B and 53C. At the point where the petal attaches, there is a large zone of between 155A and 155B. The upper surface color of the outer, intermediate and inner petals is between 53B and 45B. At the point where the petal attaches, there is a large zone of between 2D and 1D.

The under and upper surface colors of the petaloids are similar in coloration to the upper and under surfaces of the intermediate and inner petals.

The general tonality of the newly opened flower is between 53B and 45B.

THREE-DAY-OLD FLOWER

The under surface color of the outer, intermediate and inner petals is between 155A and 155B often moderately to heavily suffused with between 60B and 53C. At the point where the petal attaches, there is a large zone of between 155A and 155B. The upper surface color of the outer, intermediate and inner petals is between 53B and 45B. At the point where the petal attaches, there is a large zone of between 155A and 4D.

The under and upper surface colors of the petaloids are similar in coloration to the upper and under surfaces of the intermediate and inner petals.

The general tonality of the three-day-old flower is between 53B and 45B.

On the spent bloom, the petals usually drop off cleanly.

In October in Wasco, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 150) and are arranged regularly about the pistils; a few are mixed with petaloids. The filaments are of somewhat short to medium length (about 0.5 to about 1.2 cm.) most with anthers. Filaments are between 154D and 1D in color. The anthers are moderately small for the class and all open approximately at the same time. Anther color when immature is near 22A on the external part and near 78D on the internal part. Anther color at maturity is near 165B on the external part and near 200A on the internal part. Pollen is moderate and between 18C and 19C in color.

FEMALE REPRODUCTIVE ORGANS

Pistils vary in number (average about 75). The styles are moderately even, average in length (about 0.4 to about 0.7 cm.), somewhat thin to average in caliper, and loosely bunched to somewhat separated. Stigma color is near 11A. Style color is between 1C and 154C usually moderately suffused with between 53B and 53C. Ovaries are usually all enclosed in the calyx.

Hips are of somewhat short length (about 1.2 to about 1.5 cm.), rounded in form with a flat top, and between 28A and 30C in color when ripe. The hip surface is smooth with thick fleshy walls. The sepals are moderately permanent and usually straight in shape.

The seeds are irregularly rounded, smooth in texture, approximately 10 to about 14 per hip, about 0.4 to about 0.6 cm. in diameter at the widest point and between 164A and 165B in color.

FOLIAGE

The compound leaves are usually comprised of three to seven leaflets and are borne abundantly. The five-leaflet leaves are about 9.6 to about 14.6 cm. in length and about 7.6 to about 11.6 cm. in width at the widest point, moderately leathery to somewhat crisp in texture, and glossy in finish on the upper side and matte in finish on the underside. The leaves have a pinnate venation pattern. The terminal leaflets are about 3.9 to about 7.1 cm. in length and about 3.1 to about 4.3 cm. in width at the widest point, shaped moderately ovate to somewhat oval with acute to slightly acuminate apices and rounded to somewhat acute bases. Their margins are usually simply serrate.

The upper surface color of the mature leaf is between 139A and 137A. The under surface color of the mature leaf is between 147B and 146A. The under and upper colors of the leaf veins on the mature leaf are similar in coloration to the upper and under surfaces colors of the mature leaf. The upper surface color of the young leaf is between 137A and 146A, often heavily suffused with between 187A and 187B. The under surface color of the young leaf is between 138B and 146A, often heavily suffused with between 187B and 187A. The under and upper colors of the leaf veins on the young leaf are similar in coloration to the upper and under surfaces colors of the young leaf.

The rachis is average in caliper and rough. The upper side is deeply grooved with few hairs and stipitate glands on the edges of the grooves. The under side of the rachis is rough with few stipitate glands and small prickles. The rachis color is near 146D on the under side and near 137C on the upper side often heavily suffused on the young leaves with between 187B and 187A.

The stipules are about 1.3 to about 1.9 cm. in length and moderately wide (about 0.5 to about 0.8 cm.) with moderately long straight points that usually turn out at an angle of more than 45 degrees. The under and upper surface color of the stipule is between 137A and 137B.

The petiole is average in caliper and rough. The upper side is deeply grooved with few hairs and stipitate glands on the edges of the grooves. The under side of the petiole is rough with few stipitate glands and small prickles. The petiole is about 0.8 to about 1.6 cm. in length and about 0.1 to about 0.2 cm in width at the widest point. The petiole color is near 146D on the underside and near 137C on the upper side often heavily suffused on the young leaves with between 187B and 187A.

The plant displays a high degree of resistance to black spot, powdery mildew, downy mildew and rust as compared to other commercial varieties grown under comparable conditions in Wasco, Calif. The plant's winter hardiness and drought/heat tolerance are yet to be determined.

GROWTH

The plant has an upright bushy medium height growing habit (about 110 to about 142 cm. in height and about 108 to about 122 cm. spread at the widest point), with full branching. It displays moderately vigorous growth and the canes are of medium to somewhat heavy caliper for the class (about 1.8 to about 3.2 cm. in diameter at the widest point).

The color of the major stems is between 146A and 146B. They bear many large prickles that are about 0.6 to about 1.2 cm. in length. The large prickles are angled slightly downward with a medium length moderately narrow oval base; prickle color is between 177B and 177C. The major stem bears few small prickles of similar shape and coloration.

The color of the branches is between 137C and 146B sometimes lightly suffused with between 187A and 187B. They bear many large prickles which are of similar size and shape to the large prickles on the major stems; prickle color is between 152D and 152C often moderately suffused with between 187C and 187D. The branches bear few small prickles of similar shape and coloration.

The color of the new shoots is between 144A and 146C often heavily suffused with between 187B and 187A. They bear many large prickles which are of similar size and shape to the large prickles on the major stems; prickle color is between 152D and 152C often heavily suffused with between 187B and 187C. The shoots bear few small prickles of similar shape and coloration.

I claim:

1. A new and distinct Shrub rose plant of the variety substantially as described and illustrated herein.

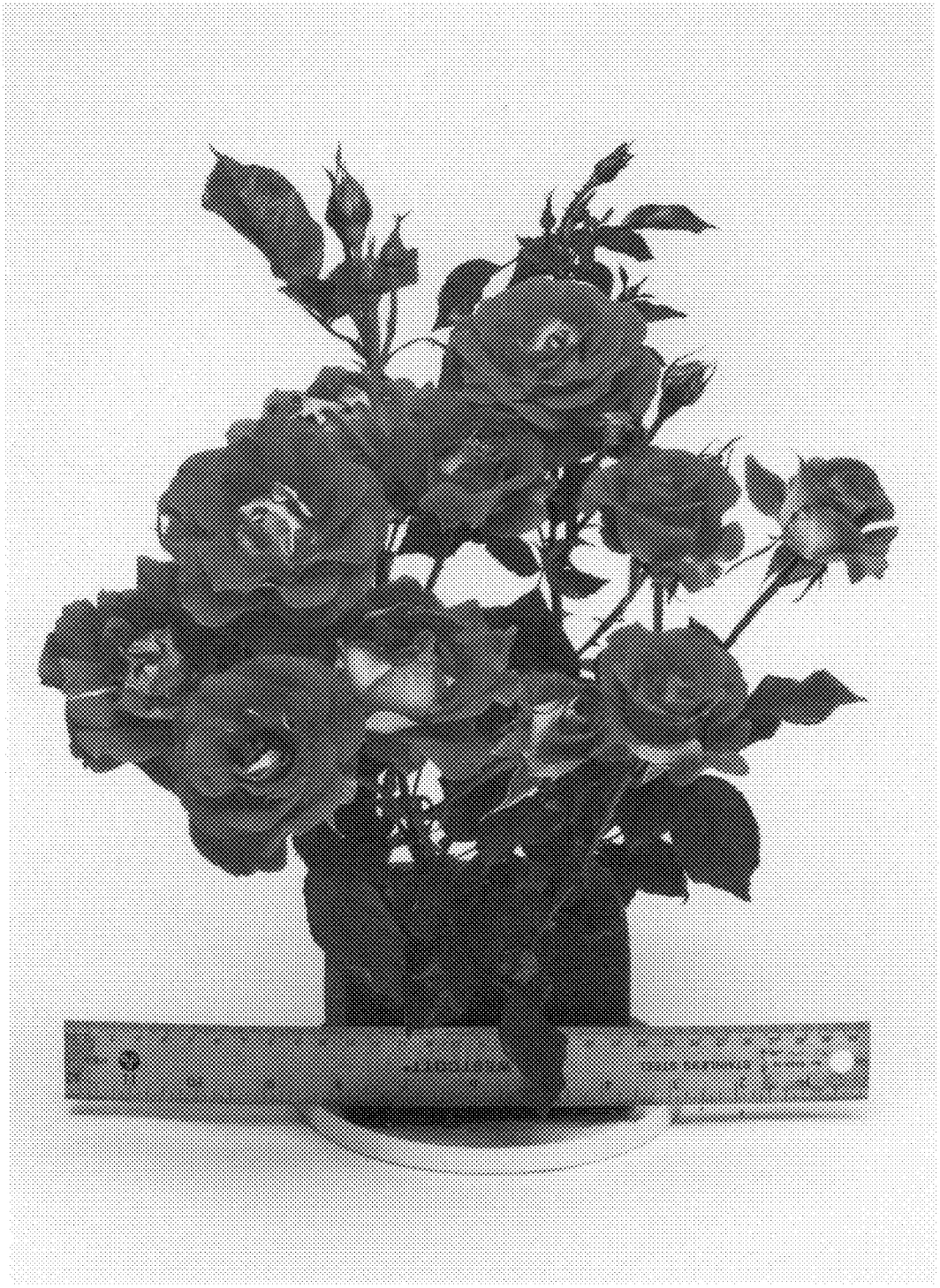

* * * * *